US012673346B2

(12) United States Patent
Lee et al.

(10) Patent No.: US 12,673,346 B2
(45) Date of Patent: Jul. 7, 2026

(54) INTERPOSER FOR AN ULTRASOUND TRANSDUCER ARRAY

(71) Applicant: Siemens Medical Solutions USA, Inc., Malvern, PA (US)

(72) Inventors: Baik Woo Lee, Issaquah, WA (US); Christopher S. Chapman, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 880 days.

(21) Appl. No.: 16/680,611

(22) Filed: Nov. 12, 2019

(65) Prior Publication Data

US 2021/0138506 A1      May 13, 2021

(51) Int. Cl.
B06B 1/02          (2006.01)
A61B 8/00          (2006.01)

(52) U.S. Cl.
CPC .......... B06B 1/0207 (2013.01); A61B 8/4461 (2013.01); A61B 8/4483 (2013.01); B06B 2201/20 (2013.01)

(58) Field of Classification Search
None
See application file for complete search history.

(56) References Cited

U.S. PATENT DOCUMENTS

| | | | |
|---|---|---|---|
| 5,527,741 A * | 6/1996 | Cole | H01L 23/5383 257/E23.173 |
| 7,304,415 B2 | 12/2007 | Petersen et al. | |

| | | | |
|---|---|---|---|
| 7,576,435 B2 * | 8/2009 | Chao | H01L 23/49833 257/774 |
| 7,795,784 B2 | 9/2010 | Davidsen | |
| 8,659,212 B2 | 2/2014 | Eggen et al. | |
| 8,754,574 B2 | 6/2014 | Morris et al. | |
| 9,067,779 B1 * | 6/2015 | Rothberg | B81B 7/007 |
| 9,180,490 B2 | 11/2015 | Tai | |
| 2006/0024861 A1 * | 2/2006 | Cordes | G01R 1/0735 438/106 |
| 2007/0222339 A1 * | 9/2007 | Lukacs | B06B 1/0622 310/334 |
| 2007/0239001 A1 * | 10/2007 | Mehi | G10K 11/341 600/437 |
| 2008/0221454 A1 * | 9/2008 | Davidsen | G01S 7/5208 600/459 |
| 2008/0273424 A1 * | 11/2008 | Wodnicki | A61B 8/0833 257/E27.107 |
| 2008/0315331 A1 * | 12/2008 | Wodnicki | B06B 1/0629 257/E27.122 |

(Continued)

OTHER PUBLICATIONS

Li, Liyi, et al. "Formation of polymer insulation layer (liner) on through silicon vias (TSV) with high aspect ratio over 5:1 by direct spin coating." 2016 IEEE 66th Electronic Components and Technology Conference (ECTC). IEEE, 2016. (Year: 2016).*

(Continued)

*Primary Examiner* — Jonathan D Armstrong

(57)          ABSTRACT

For transducer connection to an integrated circuit, a silicon or other wafer-based chip is processed to provide signal routing, such as altering the pitch using wafer process deposited conductors. This chip or silicon interposer may be more simply re-designed to relate the pitch of an array to the integrated circuit I/Os, avoiding redesign of the integrated circuit.

14 Claims, 6 Drawing Sheets

(56) References Cited

U.S. PATENT DOCUMENTS

| | | | |
|---|---|---|---|
| 2010/0025785 A1* | 2/2010 | Robinson | B06B 1/0622 |
| | | | 257/E21.575 |
| 2011/0071397 A1* | 3/2011 | Wodnicki | B06B 1/0629 |
| | | | 228/179.1 |
| 2011/0198968 A1* | 8/2011 | Sato | A61B 8/4483 |
| | | | 310/317 |
| 2011/0237952 A1* | 9/2011 | Ooishi | A61B 8/00 |
| | | | 600/459 |
| 2012/0098123 A1* | 4/2012 | Yu | H01L 23/49827 |
| | | | 257/E23.06 |
| 2012/0133001 A1* | 5/2012 | Tkaczyk | H01L 27/20 |
| | | | 438/66 |
| 2012/0143060 A1* | 6/2012 | Weekamp | B06B 1/0622 |
| | | | 216/13 |
| 2013/0020907 A1* | 1/2013 | Bernasseau | H01L 41/313 |
| | | | 29/25.35 |
| 2013/0200753 A1* | 8/2013 | Dausch | A61B 8/4444 |
| | | | 29/25.35 |
| 2013/0214641 A1* | 8/2013 | Eggen | B06B 1/0622 |
| | | | 310/314 |
| 2013/0257224 A1* | 10/2013 | Wodnicki | B06B 1/0622 |
| | | | 29/25.35 |
| 2013/0261467 A1* | 10/2013 | Dausch | A61B 8/12 |
| | | | 29/25.35 |
| 2013/0267853 A1* | 10/2013 | Dausch | B06B 1/0607 |
| | | | 600/459 |
| 2013/0315035 A1* | 11/2013 | Tai | A61B 8/4494 |
| | | | 367/140 |
| 2014/0088430 A1* | 3/2014 | Poland | A61B 8/0841 |
| | | | 600/447 |
| 2015/0013466 A1* | 1/2015 | Nakayama | G01N 29/34 |
| | | | 73/661 |
| 2015/0087991 A1* | 3/2015 | Chen | G01S 7/52025 |
| | | | 330/253 |
| 2016/0009544 A1* | 1/2016 | Rothberg | H01L 24/94 |
| | | | 257/737 |
| 2016/0038974 A1* | 2/2016 | Gubbini | B06B 1/0622 |
| | | | 367/87 |
| 2016/0271651 A1 | 9/2016 | Petersen et al. | |
| 2016/0375466 A1* | 12/2016 | Shikata | G01N 29/32 |
| | | | 310/327 |
| 2017/0028439 A1* | 2/2017 | Shih | B06B 1/0622 |
| 2017/0059530 A1* | 3/2017 | Kandori | A61B 8/4477 |
| 2017/0188995 A1* | 7/2017 | Bruestle | B06B 1/0685 |
| 2017/0238902 A1* | 8/2017 | Lee | A61B 8/4455 |
| 2017/0252777 A1* | 9/2017 | Kidwell, Jr. | H10N 30/875 |
| 2017/0365774 A1* | 12/2017 | Rothberg | H10N 30/05 |
| 2018/0140278 A1* | 5/2018 | Bromberg | A61B 8/4494 |
| 2018/0161016 A1* | 6/2018 | Choi | A61B 8/546 |
| 2018/0177490 A1* | 6/2018 | Shiraishi | A61B 8/4483 |
| 2018/0192999 A1* | 7/2018 | Song | A61B 8/145 |
| 2018/0257927 A1* | 9/2018 | Rothberg | B81C 1/00182 |
| 2018/0264519 A1* | 9/2018 | Sudol | A61B 8/12 |
| 2018/0313943 A1* | 11/2018 | Bruestle | G01N 29/2437 |
| 2018/0327256 A1* | 11/2018 | Lee | H01L 23/00 |
| 2018/0360422 A1* | 12/2018 | Rigby | G01S 15/8925 |
| 2019/0022701 A1* | 1/2019 | Choi | B06B 1/0622 |
| 2019/0027675 A1* | 1/2019 | Choi | G01N 29/2437 |
| 2019/0290243 A1* | 9/2019 | Bryzek | A61B 8/4488 |
| 2020/0009615 A1* | 1/2020 | Lee | H01L 41/1132 |
| 2020/0182930 A1* | 6/2020 | Lal | G01N 29/22 |
| 2020/0289090 A1* | 9/2020 | Iwashita | B29C 65/48 |
| 2020/0391245 A1* | 12/2020 | Barrett | H01L 41/338 |
| 2021/0069749 A1* | 3/2021 | Durocher | B06B 1/0685 |

OTHER PUBLICATIONS

Chen, Qian-Wen, et al. "Fabrication and electrical characteristics of a novel interposer with polymer liner and silicon pillars with ultra-low-resistivity as through-silicon-vias (TSVs) for 2.5 D/3D applications." Microsystem Technologies 21.10 (2015): 2207-2214. (Year: 2015).*

U.S. Appl. No. 16/181,464, filed Nov. 6, 2018.

Wildes, Douglas, et al. "4-D Ice: a 2-D array transducer with integrated ASIC in a 10-Fr catheter for real-time 3-D intracardiac echocardiography." IEEE transactions on ultrasonics, ferroelectrics, and frequency control 63.12 (2016): 2159-2173.

* cited by examiner

Integrated passives (such as decoupling capacitor for ASIC) on Si interposer

20

12

12

90 — Form Interposer with Wafer Process

91 — Connect Interposer, Array, and Integrated Circuit

92 — Test Assembled Module

11A

11B 11A
11B

Separate fabrication & test of acoustic
(upper) and electronic (lower) modules by
employing two flex circuits Combining two good acoustic (upper) and
electronic (lower) modules by employing
various bonding materials including epoxy,
ACF, solder and Ag paste

INTERPOSER FOR AN ULTRASOUND TRANSDUCER ARRAY

BACKGROUND

The present embodiments relate to interconnection of transducer arrays with electronics. Achieving the interconnection between an acoustic array and the associated transmit and/or receive electronics is a technological challenge for any transducer and particularly for multidimensional (matrix) transducers. Hundreds or thousands (e.g., up to 10,000) of different elements distributed in two dimensions (azimuth and elevation) require interconnection along the z-axis (depth or range) for at least the elements surrounded by other elements. Since the elements are small (e.g., 250-500 um), there is limited space for separate electrical connection to each element. Given the number of elements and to avoid unwieldy cables, micro-beamforming application specific integrated circuits (ASICs) to directly operate acoustic elements are thus placed as close to the acoustic elements as possible and direct signal connections have to be made from the ASICs to the acoustic elements. Thus, the pitch of ASIC input/outputs (I/Os) needs to match that of corresponding acoustic elements. The pitch of acoustic elements, however, varies depending the array design, which is based on targeted resolution, penetration, beam steering and applications (cardiac, OB/Gyn, or general imaging). It is not ideal or practical to develop new ASICs whenever new transducers come out with different acoustic pitches.

SUMMARY

By way of introduction, the preferred embodiments described below include methods, systems and components for transducer connection to an integrated circuit. A silicon or other wafer-based chip is processed to provide signal routing, such as altering the pitch using wafer process deposited conductors. This chip or silicon interposer may be more simply re-designed to relate the pitch of an array to the integrated circuit I/Os, avoiding redesign of the integrated circuit.

In a first aspect, a multidimensional transducer array system is provided. An acoustic array has transducer elements distributed in a grid over two dimensions. A silicon interposer has a first surface with conductors electrically connected to the acoustic array. The conductors extending in the silicon interposer to a second surface opposite the first surface. An integrated circuit has transmit and/or receive circuits for ultrasound scanning with the acoustic array. The integrated circuit electrically connects to the conductors on the second surface of the silicon interposer.

In second aspect, a transducer array system is provided. An acoustic array has transducer elements. A wafer chip has a first surface with conductors electrically connected to the acoustic array. The conductors extend in the wafer chip to a second surface opposite the first surface. An integrated circuit chip has transmit and/or receive circuits for ultrasound scanning with the acoustic array. The integrated circuit chip electrically connects to the conductors on the second surface of the wafer chip.

In a third aspect, a method is provided for connecting electronics with an array of acoustic elements. A wiring layer redistributing conductors is formed on a wafer with a wafer process. A wafer part with the wiring layer is connected between the array and an integrated circuit, the connecting electrically connecting the acoustic elements to pads of the integrated circuit through the wafer and wiring layer.

The present invention is defined by the following claims, and nothing in this section should be taken as a limitation on these claims. Further aspects and advantages of the invention are discussed below in conjunction with the preferred embodiments and may be later claimed independently or in combination. Different embodiments may achieve or fail to achieve different objects or advantages.

BRIEF DESCRIPTION OF THE DRAWINGS

The components and the figures are not necessarily to scale, emphasis instead being placed upon illustrating the principles of the invention.

Moreover, in the figures, like reference numerals designate corresponding parts throughout the different views.

DETAILED DESCRIPTION OF THE DRAWINGS AND PRESENTLY PREFERRED EMBODIMENTS

A wafer-based (e.g., silicon) interposer is provided for an ultrasound transducer, such as for a matrix array ultrasound transducer. The interposer or wafer chip is placed between acoustic elements and micro beamforming ASICs. The interposer may be multi-functional, not only addressing high density signal routing to redistribute ASICs I/Os pitches to any pitch of acoustic elements but also providing further benefits including reduction of ASICs' heat density, improved ASICs' interconnection joint reliability, and/or better ASICs' chip tiling process. The same design of ASIC chip can be used for different acoustic-pitched ultrasound transducers without new development of ASICs.

In one embodiment, a silicon interposer uses BEOL (Back-End-Of-Line) or RDL (ReDistribution Layers) wafer processes or fabrication on a silicon core bearing TSV (through Si via). The silicon interposer is between one or more micro beamforming ASICs and the flex circuits on top of which an acoustic array is built. The silicon interposer provides a high-density signal routing for matching acoustic-electronic I/Os pitches to 2D matrix ultrasound transducers. The flat and stiff silicon interposer structure has dimensional stability with a range of temperatures and an ultrasmooth surface finish to form sub-micron wiring structures. The silicon interposer may reduce the heat density of ASICs since the high thermally conductive interposer is in direct contact with the ASIC without any other thermal barrier layers such as flex circuits in between. The silicon interposer may allow for chip tiling due to the dimensional stability and planarity. Batch ASIC assembly processes at the wafer level may be used to create the interposer. Since fine pitch I/Os of an ASIC are redistributed to larger I/O pitches through the silicon interposer, bigger and more reliable electrical joints, such as solder balls, copper pillar bumps or Au plated bumps, may be used at this junction. These larger joints may better accommodate the thermo-mechanical stress at the joints as compared to smaller joints, resulting in improved thermo-mechanical reliability at the ASIC chip-to-flex joints.

Figure 1:
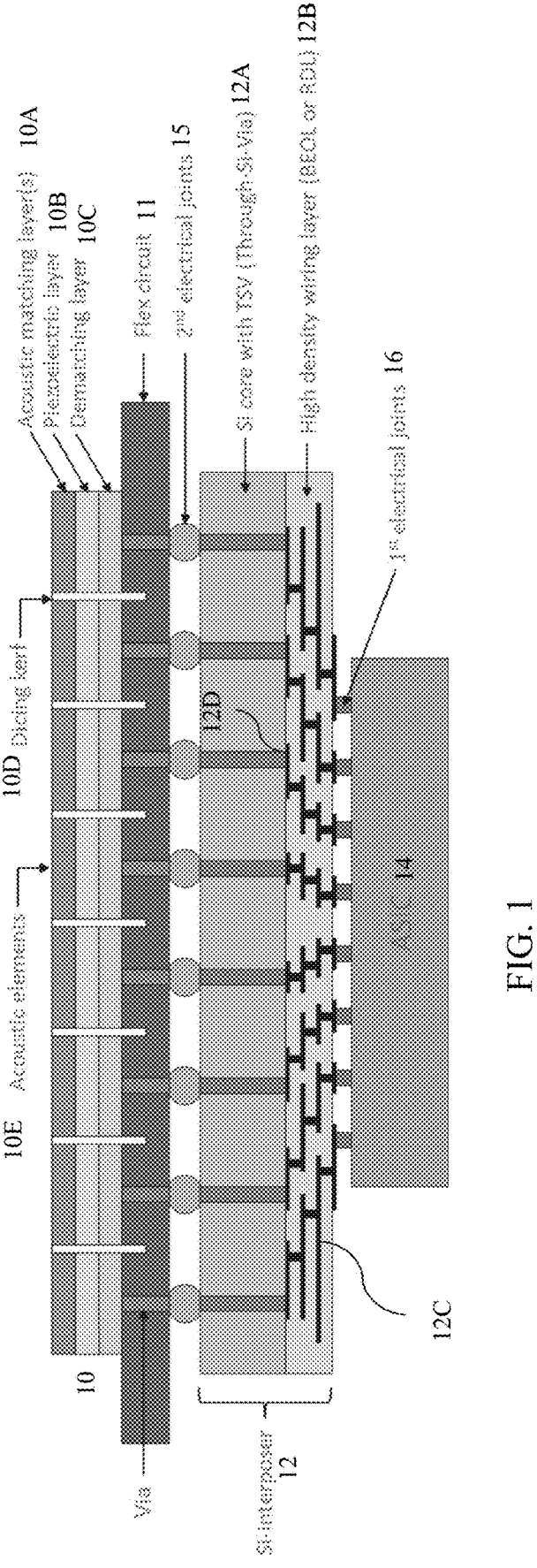
FIG. 1 is a cross-section view of one embodiment of a silicon interposer between an ultrasound array and an integrated circuit.

FIG. 1 is a cross-section view of one embodiment of a transducer array system. The system is used for an ultrasound transducer probe, such as in a handheld probe for scanning from an exterior of a patient or an intra-cavity or catheter-based probe for scanning from within a patient. The system includes a one or multi-dimensional transducer array, such as a matrix array with a distribution of elements in both azimuth and elevation. A multi-dimensional transducer array system may be provided.

The array system includes an acoustic module or array 10 formed from a transducer stack, at least one interposer 12, and at least one electronics module formed from an integrated circuit 14. The interposer 12 provides high density signal routing. The interposer 12 is placed between one or more micro-beamforming ASICs 14 and a flex circuit material 11 under the acoustic array 10. The interposer 12 provides electrical, thermal, process, reliability and acoustic benefits. Additional, different, or fewer modules may be included, such as not including the flexible circuit material or layer 11. The array system and corresponding probe are formed using the method of FIG. 9, FIG. 10, or another method.

Figure 7:
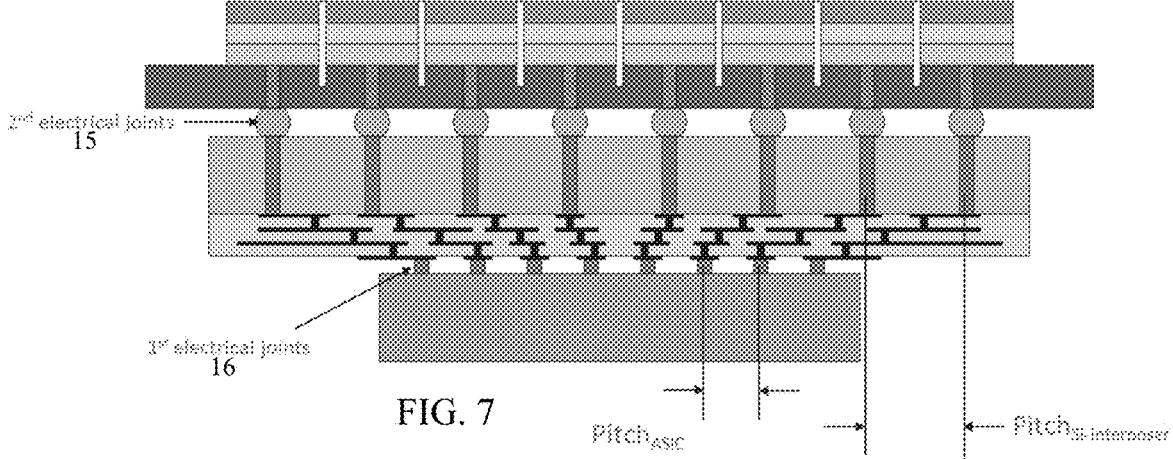
FIG. 7 is a cross-section view of another embodiment with different size electrical connectors.

The acoustic module includes the acoustic array 10, which has transducer elements 10E distributed in a grid over one or two dimensions. The multidimensional transducer array is an array of piezoelectric or microelectromechanical (capacitive membrane) elements 10E. Piezoelectric examples are used herein. The array is flat, concave or convex. In one embodiment, the elements 10E are distributed along two dimensions. The elements 10E are distributed along any of various pitches, such as every 250, 400 or 500 micrometers, in a fully sampled spacing along two dimensions. In FIG. 7, the pitch of the transducer elements 10E is shown as pitch $Pitch_{SI-interposer}$. Other pitches or a pitch that varies as a function of location may be used. The pitch may be the same or different in different directions or dimensions, such as 300 micrometers along elevation and 600 micrometers in azimuth. Full or sparse sampling of placement of the elements 10E is provided.

The array 10 of transducer elements 10E includes one or more impedance matching layers 10A, a piezoelectric layer 10B, and a de-matching layer 10C. Each of the elements 10E of the array 10 includes at least two electrodes. The elements transduce between electrical and acoustical energies. Additional, different, or fewer layers may be provided. For example, a backing block may be positioned on one side of the array 10 for limiting acoustic reflection from energy transmitted in an undesired direction. A lens, a window, or other now know or later developed multidimensional transducer array components may be included.

The matching layer 10A is a ¼ wavelength thickness layer of material. The material has an acoustic impedance between the impedance of the piezoelectric layer 10B and the patient. Multiple layers for a gradual change in acoustic impedance may be used.

The piezoelectric layer 10B is a slab or plate of piezoelectric material. A solid piezoelectric may be used. Single or poly-crystal piezoelectric material may be used. In other embodiments, a composite of piezoelectric and epoxy or another polymer is used.

The de-matching layer 10C is a ¼ wavelength thickness layer of material. Any material may be used, such as tungsten carbide or graphite. The de-matching layer 10C provides a clamped boundary condition, leading to better sensitivity and wider bandwidth in the ultrasound transducer.

A grounding plane may form one electrode. The grounding plane may be provided by a conductive matching layer 10A. Alternatively, a sheet of conductor is placed or deposited on, within, or below the matching layer 10A.

Another sheet of conductor provides conductors to form the signal electrodes. Conductor deposited on the flexible circuit material 11 may be used. Alternatively, conductors placed or formed on the piezoelectric layer 10B are positioned between the piezoelectric layer 10B and the de-matching layer 10C. In yet other embodiments, the conductor is formed by conductive material of the de-matching layer 10C. Once diced or separated by kerfs 10D, the sheet of conductor provides signal electrodes for the transducer elements 10E. An electrically separate signal electrode is provided for each transducer element 10E.

The acoustic elements 10E of the ultrasound transducer may be formed by dicing a laminate of the materials 10A-C. The dicing to form the kerfs 10D separating the elements 10E may extend into the flexible circuit material 11.

The array 10 is connected to the flexible circuit material 11. A sheet of flexible circuit material, such as a polyimide, is positioned between the array 10 and the interposer 12. Traces or other conductors may be included on and/or in the sheet, such as deposited and/or etched copper traces. Passive and/or active electronics may be attached.

The flexible circuit material 11 connects with the acoustic stack to form the acoustic module. Asperity contact is provided from the signal electrodes to traces, vias, or other conductors on and/or in the flexible circuit material 11. The physical connection is by bonding, so a layer of bonding material is provided. The bonding material may be epoxy or Ag paste. The epoxy layer holds the flexible circuit material 11 to the acoustic stack or array 10, such as holding the flexible circuit material 11 to the de-matching layer 10C.

The flexible circuit material 11 includes a plurality of vias. One via is provided for each transducer element 10E, but additional or fewer vias may be provided. The vias 20 are formed in the flexible circuit material 11, such as by etching, deposition, drilling, or molding. A conductor, such as copper, lines or fills a hole to create a conductive path through a thickness of the flexible circuit material 11. This via 20 provides an electrically conductive path from one side of the flexible circuit material 11 to the other side, such as to allow electrical connection from the signal electrodes of the elements 10E to the interposer 12.

Figure 11:
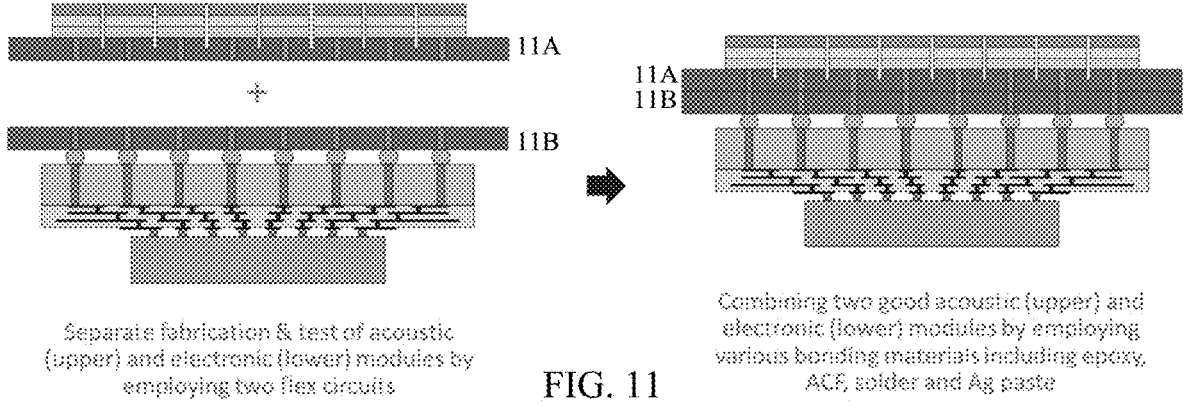
FIG. 11 illustrates an embodiment of a method for connecting using modules.

In other embodiments, more than one layer of flexible circuit material 11 is provided. For example, a stack of two layers of flexible circuit material is provided between the silicon interposer 12 and the acoustic array 10. FIG. 11 shows one example with two layers 11A, 11B of flexible circuit material.

The interposer 12 is a wafer chip or wafer processed substrate 12A. A wafer, after processing to add the wiring layers or conductors, is singulated to form the wafer chip. Any substrate material may be used, such as silicon, other semiconductor, or glass material. The examples used herein are silicon. The singulated chip from the wafer is sized to match, be larger, or be smaller than a surface area of the array 10.

The wafer chip forming the interposer 12 has two opposing surfaces. One surface is placed adjacent to and/or in contact with the array 10 or the flexible circuit material 11. At least part of the opposing surface is placed adjacent to and/or in contact with the integrated circuit 14. The opposing surfaces include exposed conductors, such as electronic contact or I/O pads. The conductors on one surface route and extend to the other surface.

At least part of the conductors extending through the interposer 12 are vias 12D. One via 12D is provided for each transducer element 10E, but additional or fewer vias 12D may be provided. The vias 12D are formed in the interposer 12, such as by etching, deposition, drilling, or molding. A conductor, such as copper, lines or fills a hole to create a conductive path through all or part of a thickness of the interposer 12. The vias 12D provide an electrically conductive path from one side of the interposer 12 to the other side or from one side to a wire routing layer 12B of the interposer 12, such as to allow electrical connection from the signal electrodes of the elements 10E to the electronics module (e.g., integrated circuit 14).

The vias 12D are positioned to connect with the signal electrodes. Where the vias 21D are at a same pitch Pitch$_{Si\text{-}interposer}$ as the signal electrodes and corresponding transducer elements 10E, the vias 12D are aligned with the signal electrodes (see FIG. 7). In the example of FIG. 1, the vias 12D of the interposer 12 have a same pitch. The pitch of the vias 12D may be different than the pitch of the signal electrodes. In this case, a trace or pad is formed on the interposer 12 to route signals from the signal electrodes to the vias 12D. Alternatively, the vias 12D are angled so that the pitch is provided on the surface adjacent to the signal electrodes and a different pitch is provided on the opposite surface of the interposer 12.

Once aligned and bonded, the signal electrodes electrically connect to the vias 12D of the interposer 12. This provides for z-axis routing of signals from the transducer elements 10E to or from the electronics module (e.g., integrated circuit 14). The assembled acoustics module includes the bonding material used to physically hold the interposer 12 to the transducer elements 10E with electrical connection by asperity contact.

Since the pitch of the contact pads of the integrated circuit 14 may be different than the pitch of the electrodes of the elements 10E of the array 10, the conductors of the interposer 12 are routed within or on the interposer 12 to alter the pitch. For example, FIG. 7 shows the pitch, Pitch$_{ASIC}$, for the ASIC 14 as smaller than the pitch, Pitch$_{Si\text{-}interposer}$, for the elements 10E. Any ratio may be provided. The pitch ratio may be uniform along one or both dimensions. The pitch ratio may be the same or vary along a dimension and/or between dimensions.

Any conductor routing in a semiconductor or other wafer may be used to route the conductors to provide the desired pitch. In the example of FIG. 1, one or more routing layers 12B for routing traces 12C are provided to alter the pitch. While shown on the side or surface adjacent to the integrated circuit 14, the routing layers 12B may be on opposite sides or the opposite side. The routing or wiring layer or layers 12B are a conductor distribution layer altering from the pitch of the transducer elements 10E to a pitch of pads of the integrated circuit chip 14. The conductors extend in the silicon interposer 12 from one surface to an opposing surface. The conductors include the vias 12D and electrically connected traces 12C.

Any semiconductor fabrication or wafer process may be used to form the conductors and/or routing layers 12B. For example, fine pitch signal routing on the surface of the Si-interposer 12 is achieved by either BEOL (Back-End-Of-Line) or polymer-based Cu RDL (ReDistribution Layers). BEOL fabrication is based on single or dual Cu damascene process with inorganic dielectric materials, e.g., SiO2, Si3N4, or low-K materials. The polymer-based Cu RDL (redistribution layers) process uses a semi-additive process to form Cu conducting traces and photo-patternable polymer materials as the dielectric insulating layer. Other deposition, etching, patterning, or wafer process may be used. Wafer process layers 12B are formed on the interposer 12.

The traces 12C are formed to alter the pitch. The conductors change from a pitch of the elements 10E to a pitch of the electrodes or electrical contact pads of the integrated circuit 14. For example, the Si-interposer 12 matches the pitch of ASIC 14 I/Os to that of acoustic array elements 10E. In 2D matrix ultrasound transducers, the ASICs 14 drive acoustic elements 10E and receive the signals from the elements 10E. A few thousands or up to ten thousands of signal connections are made from ASICs 14 directly to the acoustic elements 10E. The pitch of acoustic elements 10E varies depending the transducer or array design, such as varying based on targeted resolution, penetration, beam steering, and applications (cardiac, OB/Gyn, or general imaging) of the ultrasound transducers. Rather than developing new ASICs 14 whenever new transducers come out with different acoustic pitches, the interposer 12 is used to alter pitch.

In one embodiment, the Si-interposer 12 is a substrate 12A bearing through-silicon-via (TSV) 12D. The core is made of silicon wafer in the middle and high-density routing layers 12B formed on either one surface or both front and back surfaces of the silicon core. The smooth surface of the semiconductor (e.g., Si) provides planar controllability for high density wiring. TSVs 12D are manufactured using the traditional Bosch etch, sub-atmospheric chemical vapor deposition (SACVD) isolation oxide, physical vapor deposition (PVD) Ta barrier/PVD Cu seed, followed by electroplating Cu in sequence.

Figure 2:
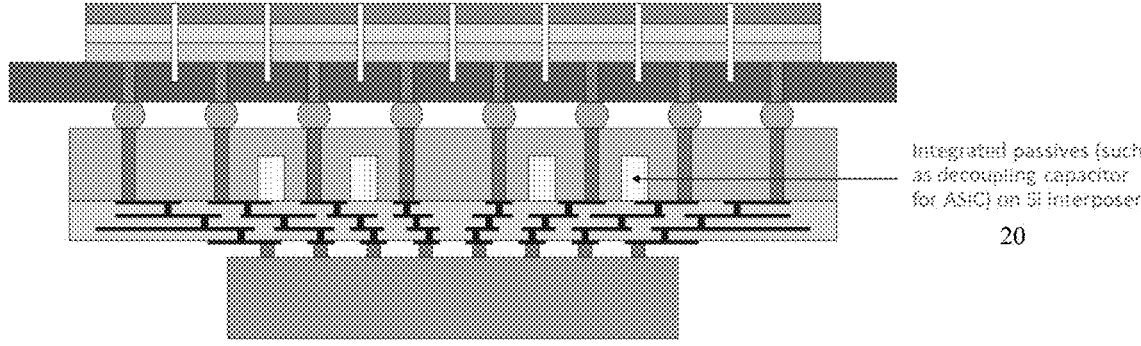
FIG. 2 is a cross-section view of another embodiment with passive components in the silicon interposer.

FIG. 2 shows another embodiment of the interposer 12. Since a semiconductor 12A is used for the interposer 12, one or more passive electrical components 20 are integrated within the interposer 12 and are electrically connected to the integrated circuit 14. Various passive components 20 may be integrated into the interposer 12, allowing placement of passives as close to ASICs 14 as possible. Any passive component may be provided, such as a capacitor, resistor, or inductor. In the case of integrated decoupling capacitors, the Si-interposer 12 may be fabricated to have parallel metal conductors with an insulator in between them or trench capacitors such as is employed with DRAM technology. This decoupling capacitor, being directly placed under the ASIC 14 with very short chip-to-chip interconnections, may significantly reduce signal noises with low-inductance decoupling for simultaneous switching compared to off-chip discrete capacitors mounted on flex circuits.

The integrated circuit 14 may be an application specific integrated circuits, analog circuit, digital circuit, switch, multiplexer, controller, processor, digital signal processor, field programmable gate array, or other now known or later developed active electrical component. The integrated circuit 14 may be in a chip form as an integrated circuit.

The active electrical components are semiconductors, such as transistors devices. "Active" electrical component is used to convey a type of device rather than operation of the device. Transistor based or switch-based devices are active while resistors, capacitors or inductors are passive devices. The active electrical devices are one or more integrated circuits 17, such as an ASIC.

The semiconductors or active electronics include transmit and/or receive circuits for ultrasound scanning with the acoustic array 10. For example, a plurality of transmit circuits are provided as semiconductors chips, a plurality of receive circuits are provided as semiconductor chips, and a controller is provided as a semiconductor chip. The transmit components are separate from or may be integrated with the receive components. Transmit components include high voltage pulsers, filters, memories, delays, phase rotators, multipliers, combinations thereof or other now known or later developed transmit beamformer component. The receive components include filters, amplifiers, delays, summers, combinations thereof or other now known or later developed receive beamformer components. Since receive beamformer components may operate at lower voltages than the transmit components, the receive and transmit components are separate devices (e.g., separate chips or integrated circuits), but a combination device for the transmit and receive operation may be provided. The integrated circuit 14 includes all or part of a transmit beamformer, pulsers, receive beamformer, amplifiers, phase rotators, delays, summers, or other active electronics used for ultrasound scanning.

The semiconductor chip or integrated circuit 14 includes input/output (I/O) pads. The semiconductor chip includes I/O conductors exposed on a largest surface. In alternative embodiments, the pads exit the chip alongside edges and are routed by wire bond or flexible circuit to a distribution on the largest surface. In other alternative embodiments, the interposer 12 routes to the conductors of the integrated circuit 14 on the sides of the chip.

The I/O pads are conductors formed on the integrated circuit 14. Cu pillars, electrodes, traces, vias, or other conductive structures may be used for the input/output pads.

The I/O pads have a pitch, Pitch$_{ASIC}$. The pitch of the I/O pads is different than a pitch of the elements 10E. In a Cartesian grid, the pitch along one dimension (e.g., azimuth) may be 500 micrometers and the pitch along another dimension (e.g., elevation) may be 400 micrometers. Other pitches may be used for either the elements 10E or the I/O pads.

The interposer 12 is bonded to the integrated circuit 14. Epoxy or other bonding material holds the interposer 12 to the integrated circuit 14. The bonding material may additionally form an electrical connection between the input/output pads and the conductors (e.g., traces 12C) of the interposer 12. For example, an anisotropic conductive film (ACF) or solder is used. In one embodiment, Cu pillar bump joints (e.g., Sn—Ag—Cu composition) with solder caps are used for ASIC chip interconnection with the interposer 12. The ASIC 14 is faced-down placed on to the interposer 12. The joints are formed to the pads (cap of Cu pillar bump joints) of the interposer 12 by high temperature reflow to melt the solder cap, such as a temperature >250° C. After heating, the bonding material is formed bonding the interposer 12, as aligned, with the integrated circuit 14. Other connections for physical and/or electrical connection may be used, such as asperity contact with an epoxy bond.

Using solder bumps, asperity contact, or other chip-to-chip connection results in the wafer chip or interposer 12 directly contacting the integrated circuit chip 14. Some air may intervene while providing the direct connection through the solder. Indirect connection may be provided, such as with one or more intervening layers of material.

In one embodiment, the Si-interposer 12 reduces the heat density of ASICs 14. The micro-beamforming ASICs 14 generate significant heat during transmitting high voltage signals to the acoustic elements 10E. The Si-interposer 12, being in direct contact with ASICs 14 without any thermal insulation layer such as flex circuits (0.12 W/mK) having very low thermal conductivity in between, has a high thermal conductivity (150 W/mK). The interposer 12 is a good heat spreader for the ASICs 14, reducing the heat density in the ASICs 14 roughly by half if the same thickness of Si-interposer 12 as ASICs 14 is employed. Additionally, the temperature gradient from ASICs 14 to the acoustic elements 10E becomes lower with the Si-interposer 12 in the thermal path, so a lesser amount of heat from the ASIC 14 will be transferred to the acoustic array 10.

Figure 3:
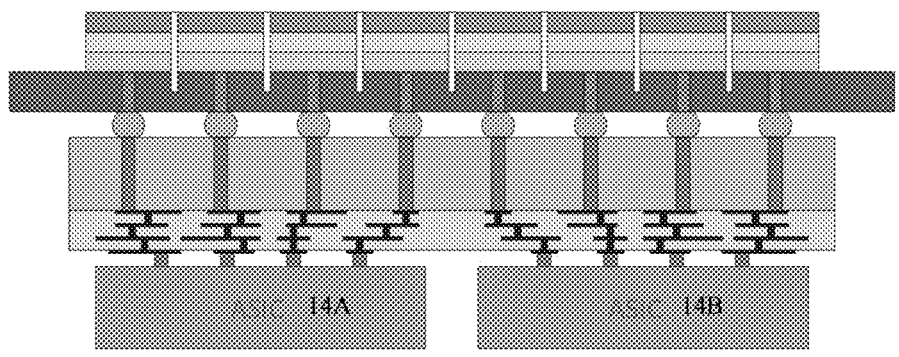
FIG. 3 is a cross-section view of another embodiment with integrated circuit tiling.

FIG. 3 shows an embodiment where two or more tiled chips 14A, 14B connect with the same interposer 12. In one embodiment, a single chip or ASIC 17, is provided as shown in FIG. 1. A larger number of acoustic elements 10E and corresponding aperture result in a larger sized ASIC chip to handle the acoustic signals. A larger ASIC chip is more expensive since the larger chip has more chances to have defects during semiconductor processing. To reduce the size of the integrated circuit 14, two or more integrated circuits 14A, 14B may be tiled. FIG. 3 shows an example where two semiconductor chips or integrated circuits 14A, 14B are used. Two or more semiconductors may be tiled or placed adjacent each other. Each semiconductor or integrated circuit 14A, 14B is positioned adjacent to the same interposer 12. Two or more smaller sized chips instead of single large expensive ASIC chip are mounted onto the interposer 12. Each integrated circuit 14A, 14B electrically connects with different sub-sets of the transducer elements 10E and corresponding conductors of the interposer 12. For example, four ASICs 14 electrically connect to four groups of elements 10E where each element 10E is in only one group. The Si-interposer 12 has good dimensional stability due to the rigidity and planarity of the substrate.

Figure 4:
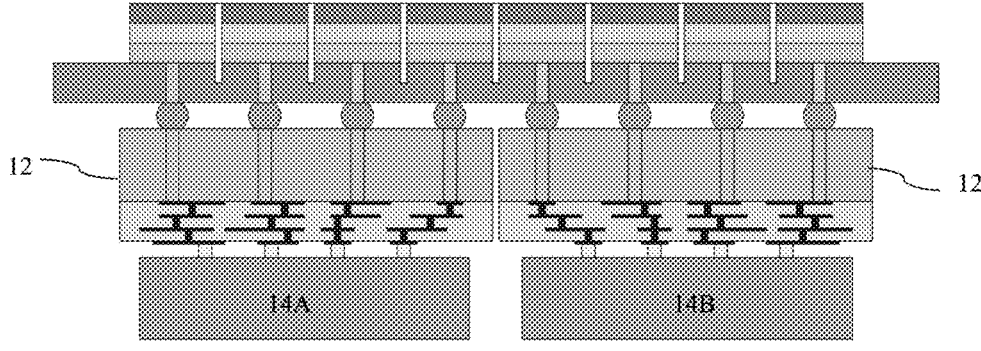
FIG. 4 is a cross-section view of another embodiment with tiling of the silicon interposer.

Multiple interposers 12 may be provided. For example, interposers 12 are stacked or sandwiched between the array 10 and the integrated circuit 14. As another example, the interposers 12 are tiled. FIG. 4 shows an example where two interposers 12 are tiled side-by-side. In the example of FIG. 4, the integrated circuits 14A, 14B are also tiled 1-to-1 with the interposers 12. In other embodiments, other ratios of tiling than 1-to-1 between the interposers 12 and the integrated circuits 14 are provided. As the size of interposer 12 increases with increasing acoustic aperture, fabrication of single big interposer 12 with high-density wiring formed thereon may result in poor yield. The tiling to utilize smaller sized interposers 12 may lead to better process yield in interposer fabrication.

Figure 5:
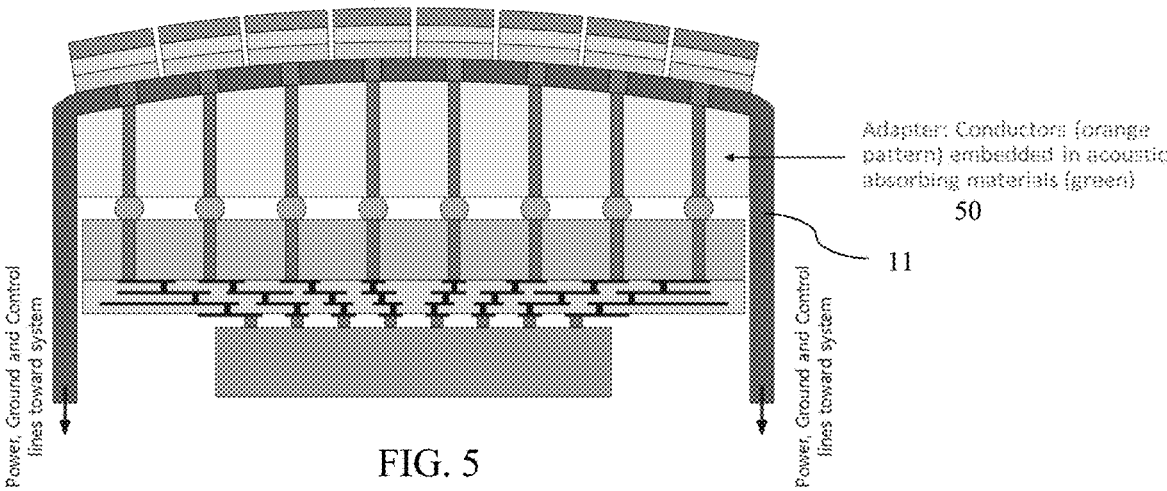
FIGS. 5 and 6 are cross-section views of other embodiments with adaptors for a curved array.
Figure 6:
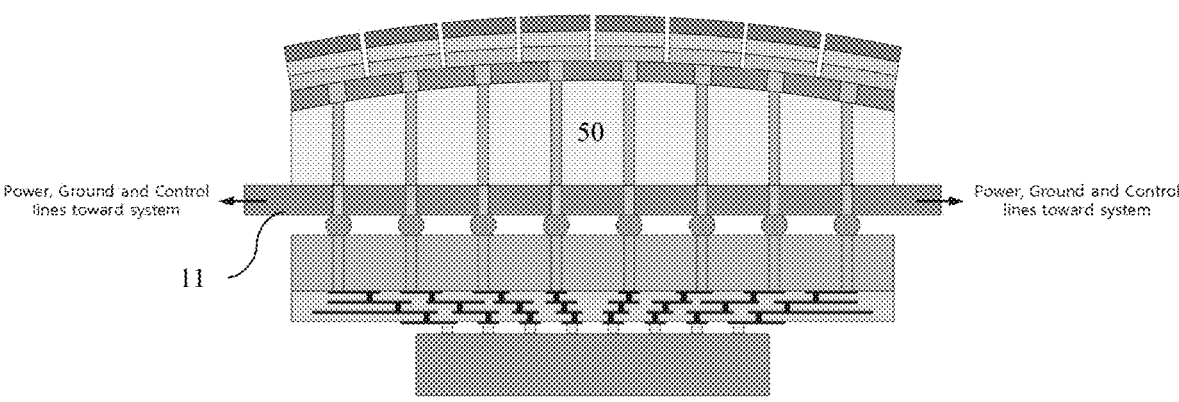

Since the interposer is planar or flat, the array 10 may be flat or planar. In other embodiments, the array 10 is curved along azimuth and/or elevation. FIGS. 5 and 6 show two examples. A adaptor 50 is positioned against the array 10, such as between the array 10 and the flexible circuit material 11 and/or interposer 12. The adaptor 50 has a curved surface on which the acoustic array 10 rests as a curved array. The adapter 50 has straight electrical conductors embedded in acoustic absorbing materials (e.g., epoxy or silicone with a metal or ceramic filler). The surface of the adaptor 50 facing with acoustic array 10 is machined to have curvature as desired.

Different positioning of the flexible circuit material 11 may be used. In the embodiment of FIG. 5, the power, ground and control signals for and/or from the ultrasound system are routed through the flex circuit material 11 on which the acoustic layers (i.e., array 10) is built. In this configuration, only a single layer of flex circuit is used to build the curved array. In addition, the integration of a decoupling capacitor in the Si-interposer 12 provides an opportunity for better power integrity for the ASIC 14 compared to capacitors mounted on long flex circuits. In the embodiment of FIG. 6, an additional flex circuit material 11 for routing of power, ground and control lines toward the ultrasound system is placed between the adapter 50 and the Si-interposer 12. Other arrangements may be provided.

Improved thermo-mechanical reliability may be provided. FIG. 7 shows an example where electrical joints 15 on the array facing surface of the interposer 12 are larger than electrical joints 16 on the opposing surface facing the integrated circuit 14. Thermo-mechanical stress at the chip-to-flex electrical joints 15, arising from CTE (Coefficient of thermal expansion) mismatch between Si-chip (3 ppm/oC) and Polyimide/Cu layered flex circuits (18 ppm/oC) while ASICs 14 are being operated to emit heat, is a reliability concern. Since fine pitch I/Os of the ASIC 14 (electrical joints 16 at $\text{Pitch}_{ASIC}$) are redistributed to larger I/O pitches (electrical joints 15 at $\text{Pitch}_{Si-interposer}$) through the Si-interposer 12, larger and more reliable electrical joints 15, such as solder balls, copper pillar bumps or Au plated bumps, may be used than for the joints 16 from the interposer 12 to the integrated circuit 14. The larger joints 15 may better accommodate the thermal stress, resulting in improved thermo-mechanical reliability at the joints 15.

Crosstalk between acoustics and electronics may be also improved. The acoustic signals between elements 10E are separated by the electrical joints 15, such as solder balls located in between the flexible circuit material 11 and the Si interposer 12. The stand-off height may be at least about 100 um. The spacing between solder balls could be air, which suppresses lateral propagation of unwanted ultrasound waves, or very low electrical modulus underfill materials.

Figure 8:
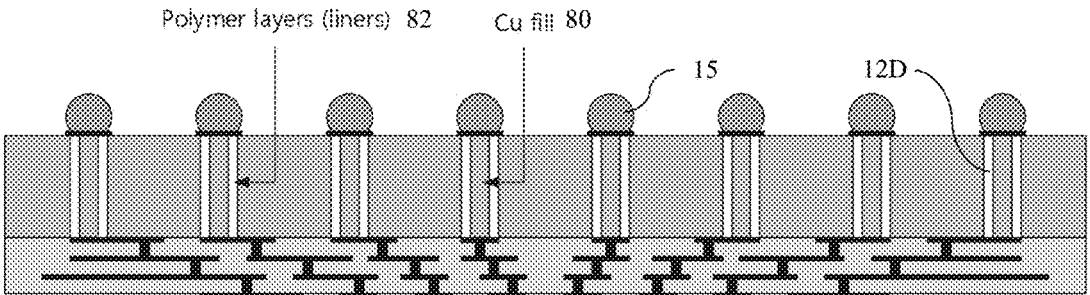
FIG. 8 is a cross-section view of an embodiment of the interposer with via liners.

FIG. 8 shows an embodiment to further reduce crosstalk. In addition to the solder balls for the joint 15, the vias 12D include a liner 82. The liner is formed from polymer with a lower elastic modulus than the interposer 12 substrate 12A or Cu filler 82 of the vias 12D. The polymer coats the inside of the vias 12D and is then filled with conductor 82.

The formed array system is placed in a housing and electrically connected to cables or other conductors for signaling with an ultrasound scanner or image processor. To control scanning and/or to receive data from scanning to generate an image of a patient scanned with the array 10, signals are provided to or from the ultrasound imaging system or scanner. The signals from the elements 10E route to the ASIC 14, which performs partial or full beamforming. Traces on the interposer 12 route signals (e.g., via traces and/or vias) to or from the integrated circuit 14 to control the scanning and/or to receive ultrasound data from the scanning. The output of the ASIC 14 is provided to the ultrasound imaging system for imaging via cables or other conductors.

Figure 9:
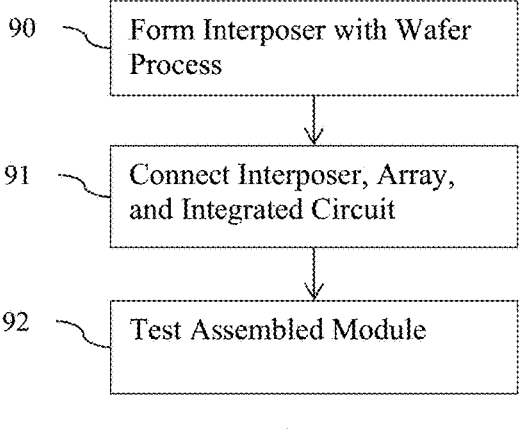
FIG. 9 is a flow chart diagram of one embodiment of a method for connecting electronics with an array of acoustic elements.

FIG. 9 shows a flow chart of one embodiment of a method for connecting electronics with a multidimensional or another array of acoustic elements. A silicon, another semiconductor, or another glass substrate is used as an interposer in a transducer. The stiff and flat interposer routes signals from the array to an integrated circuit.

The method forms any of the array systems of FIGS. 1-8 or another array system. The method is implemented as a manufacturing of the array system and/or probe. A technician or robot stacks and aligns, such as using guide posts or a frame. An oven, iron, induction solderer, press, or wave bath is used to bond or interconnect. A frame, housing, or holder are used to shape and position in a probe housing.

Additional, different, or fewer acts may be used. For example, act 92 is not performed. The acts are performed in the order shown or other orders. As another example, the testing may be divided into separate testing of an acoustic stack of the array and flex circuit and of an electronics stack of the interposer and integrated circuit. Further testing once the separate stacks are connected may be performed.

Figure 10:
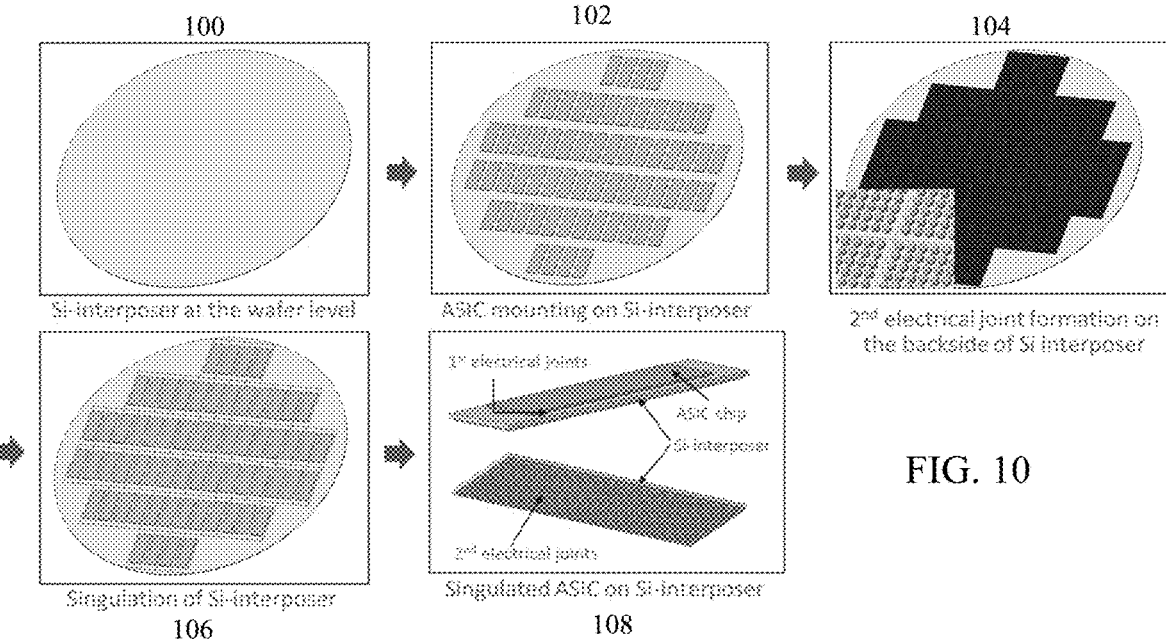
FIG. 10 illustrates another embodiment of a method for connecting electronics with an array.

In act 90, the interposer is formed. A wafer of substrate, such as silicon, is processed to form the interposer. For example, FIG. 10 shows a silicon wafer 100. Semiconductor or wafer fabrication processes are performed to form the interposer.

Vias are formed, such as using any TSV forming process, etching, or other wafer fab process. A wiring layer redistributing conductors from one pitch to another pitch is formed on the wafer using a wafer process. For example, BEOL or RDL deposits, forms, and/or etches traces over any number of dielectric or polymer material layers. For example, a single or dual Cu damascene process is used. As another example, a semi-additive process forms Cu conducting traces and photo-patternable polymer materials as the dielectric insulating layer. Other wafer processing to create the conductors on and/or in the wafer substrate may be used.

In act 91, the interposer is connected to the array and integrated circuit. The interposer is singulated from the wafer and connected. Alternatively, one or more of the connections are performed at the wafer level. The assembly of ASICs on a Si-interposer may be performed at the wafer-level. This wafer level assembly is a batch process using high quality semiconductor equipment, leading to high process yield and significant cost reduction. For example, FIG. 10 shows connecting singulated ASICs to the wafer with the formed interposers in wafer form. The ASICs are placed on to the Si-interposer at the wafer-level.

The first electrical joints (e.g., joints 16 of FIG. 1) are formed. Solder reflow, asperity contact with bonding, or another electrical and/or physical connection is formed. Polymer or other material for interconnection physically and/or electrically is added to or provided on the stack. For example, Ag paste is deposited on the interposers of the wafer and Cu pillars are provided on the integrated circuit chips. Interconnection for ASIC to Si-interposer ($1^{st}$ interconnection) and/or Si-interposer to flex ($2^{nd}$ interconnection) may be made by solder reflow, ACF (Anisotropic Conductive Film), TC (Thermal Compression) bonding, or another chip-to-chip connection.

For connection to the array, other joints may be formed at the wafer level. For example, Cu pillars or solder bumps are formed on a back-side of the interposer wafer or interposer opposite to the side to which the ASICs are mounted. FIG. 10 shows an example at 104. In alternative embodiments, the joints are formed on the backside before mounting the ASICs.

Once these electronics modules of the ASICs and interposers are formed at the wafer level, the modules may be singulated. FIG. 10 shows an example where a plurality of interposers and mounted ASICs are formed by cutting each stack from the wafer, resulting in the singulated ASIC on an Si interposer with joints for connecting to the array at 108.

These modules may be tested. For example, the modules are tested for operation of the ASICs and/or for signal routing (i.e., conductivity through the interposer to the ASIC). In other embodiments, the testing of the ASIC assembly is performed at the wafer level prior to singulation. The testing may use the electrical joints (e.g., solder bumps) to be used for connection with the array.

The array may be formed prior to connection to the interposer. For example, an acoustic module of the array with the flexible circuit material is formed for connection with the interposer.

The acoustic layers (e.g., matching, electrodes, piezoelectric, and de-matching) are stacked with or without the flexible circuit material. Using posts and/or a frame, the layers of the acoustic module are aligned and positioned against each other. The layers of the transducer are stacked as not yet bonded together. Alternatively, the layers of the transducer are previously bonded together and stacked as a unit against the flexible circuit material layer.

Polymer, paste, or other material for bonding is added to the stack, such as between and/or around layers of the stack. For example, the bottom layer of the transducer (e.g., de-matching layer) and/or the flexible circuit material layer are coated with epoxy. Other low temperature (e.g., below a Curie or breakdown temperature of part of the acoustic module) curable polymers may be used. The stack may be pressed together by a vise to form asperity contact for electrical connections. The compressed stack is heated, such as being positioned in an oven. Alternatively, the transducer stack is separately cured, and then the flexible circuit material layer is connected.

The transducer stack is diced. A saw or laser is used to form kerfs in the stack, separating the stack into transducer elements. The dicing forms the array of acoustic elements from the piezoelectric slab. The dicing may extend into the flexible circuit material, such as to separate a conductive plane on the interposer into signal electrodes. Alternatively, the dicing and resulting kerfs do not extend to the flexible circuit material or are performed prior to connection to the flexible circuit material layer.

The acoustic stack is connected to the interposer. The joints on the interposer are used to join with the vias and/or contact pads of the flexible circuit material. Solder reflow, ACF (Anisotropic Conductive Film), TC (Thermal Compression) bonding, another chip-to-chip connection, asperity contact with bonding, or another electrical and/or physical connection is formed. Polymer or other material for physical and/or electrical interconnection is added to or provided on the stack.

Once the joints join the flexible circuit material to the interposer, electrical connection from the elements to the ASIC is provided. The acoustic elements electrically connect to pads of the integrated circuit through the wafer and wiring layer of the interposer.

In one embodiment of the connecting of act 91, one or more ASICs are first mounted onto the Si-interposer, and then this assembly is electrically interconnected to the bottom surface of flex circuits. The ultrasound acoustic elements are built on the opposite side of flex circuits prior to connection to the Si-interposer. In the Si-interposer, high-density routing layers, such as BEOL and RDL, are formed to redistribute several thousands of ASIC I/Os to various pitches of the acoustic elements. The routing layers are formed on the surface of Si core because of silicon's excellent dimensional stability with temperatures and ultrasmooth surface finish to form sub-micron wiring structures. Therefore, the same ASIC chip can be used for different acoustic-pitched ultrasound transducers without new development of ASICs.

FIG. 11 shows another embodiment where multiple layers 11A, 11B of flexible circuit material are used. One layer 11A is stacked and bonded with the array 10. Another layer 11B is stacked and bonded with the interposer 12. After these separate connections are made, the layers 11A, 11B of flexible circuit material are physically and electrically connected together, such as through bonding in asperity contact. Vias and/or electrical contact pads are aligned to form electrical conductors from the elements 10E to the I/O pads of the integrated circuit 14.

In one embodiment, modular assembly is provided using these two flex circuits: one for acoustic array and the other for ASIC. Acoustic array and ASICs are separately assembled on each flex circuit and tested. Known good modules are combined to get full module. Interconnection for ASIC to Si-interposer ($1^{st}$ interconnection) and Si-interposer to flex ($2^{nd}$ interconnection) may be made by solder reflow, ACF (Anisotropic Conductive Film), TC (Thermal Compression) bonding, or another chip-to-chip connection. These processes usually happen at higher temperature than piezoelectric layers in the acoustic stack or bonding materials (e.g., epoxy) used for stacking up acoustic layers can endure. With a way to separately fabricate modules, thermal budget for ASIC assembly is not limited. Low temperature epoxy that is the same as used for building acoustic array is used for combining these two modules.

Referring again to FIG. 9, the assembled module is tested in act 92. The electrical connections from the acoustic elements to the ASIC are tested. Any sub-modules, such as an acoustic model and/or ASIC module, may be separately tested prior to stacking and bonding. The whole may be tested after stacking and bonding. The test may be for bonding strength or another physical test. The test may be for acoustic operation. Electric operation may be tested. Other testing may be performed.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A multidimensional transducer array system, the system comprising:

an acoustic array having transducer elements distributed in a grid over two dimensions;

a silicon interposer having a first surface with conductors electrically connected to the acoustic array, the conductors extending in the silicon interposer to a second surface opposite the first surface, the silicon interposer comprising a conductor distribution layer having deposited wiring in multiple layers interconnected by vias extending only part of a depth through the conductor distribution layer as part of electrical paths extending entirely through the conductor distribution layer, the deposited wiring in the multiple layers and vias forming the conductors within the conductor distribution layer, the conductor distribution layer changing the conductors from a pitch of the elements to a pitch of pads of the integrated circuit;

a flexible circuit material positioned between the acoustic array and the silicon interposer, the flexible circuit material having vias connecting from the elements to the first surface;

an integrated circuit having transmit and/or receive circuits for ultrasound scanning with the acoustic array, the integrated circuit electrically connected to the conductors on the second surface of the silicon interposer; and an adaptor between the acoustic array and the silicon interposer, the adaptor having a curved surface on which the acoustic array rests as a curved array.

2. The multidimensional transducer array system of claim 1 wherein the conductors include vias formed in a silicon wafer portion of the silicon interposer, the silicon wafer portion adjacent the conductor distribution layer of the silicon interposer.

3. The multidimensional transducer array system of claim 1 wherein the conductor distribution layer having the deposited wiring comprises wafer process layers as the multiple layers, the wafer process layers formed with a back-end-of-line or redistribution layer wafer fabrication.

4. The multidimensional transducer array system of claim 1 wherein the transducer elements are separated by kerfs and each comprise a matching layer, a piezoelectric, a de-matching layer, and a signal electrode, the signal electrodes electrically connected to the conductors.

5. The multidimensional transducer array system of claim 1 wherein one or more passive electrical components are integrated within the silicon interposer and are electrically connected to the integrated circuit.

6. The multidimensional transducer array system of claim 1 wherein the integrated circuit comprises two or more tiled chips connected with the silicon interposer.

7. The multidimensional transducer array system of claim 1 wherein the silicon interposer comprises two or more tiled chips.

8. The multidimensional transducer array system of claim 1 wherein two layers of the flexible circuit material are between the silicon interposer and the acoustic array.

9. The multidimensional transducer array system of claim 1 wherein electrical joints on the first surface are larger than electrical joints on the second surface.

10. The multidimensional transducer array system of claim 1 wherein the integrated circuit is in direct contact with the silicon interposer.

11. The multidimensional transducer array system of claim 1 wherein the silicon interposer has vias with polymer liners.

12. A method for connecting electronics with an array of acoustic elements, the method comprising:

forming a wiring layer redistributing conductors, the wiring layer formed on a wafer with a wafer process comprising back-end-of-line or redistribution layer, the wafer having vias at constant pitch through the wafer, the wiring layer changing the pitch;

connecting a flexible circuit material to a wafer part of the wafer opposite the wiring layer and to the array;

connecting the wiring layer to an integrated circuit, the connecting electrically connecting the acoustic elements to pads of the integrated circuit through the wafer and wiring layer, wherein connecting the wiring layer comprises connecting the wiring layer to the integrated circuit, and then connecting the wafer part to the flexible circuit material.

13. The method of claim 12 wherein connecting the flexible circuit material to the array comprises connecting the array to a first flexible circuit material, connecting the wafer part to a second flexible circuit material, and connecting the first flexible circuit material to the second flexible circuit material.

14. The method of claim 12 wherein forming the wiring layer comprises forming capacitors on the wafer, the capacitors connected with the integrated circuit as part of connecting the wafer part between the array and the integrated circuit.

* * * * *